United States Patent
Garault et al.

(10) Patent No.: US 11,160,289 B2
(45) Date of Patent: Nov. 2, 2021

(54) STREPTOCOCCUS THERMOPHILUS FOR USE IN PREPARATION OF FERMENTED PRODUCTS

(71) Applicant: COMPAGNIE GERVAIS DANONE, Paris (FR)

(72) Inventors: Peggy Garault, Montlhéry (FR); Laurent Marchal, Villemoisson sur Orge (FR); Marie-Agnes Souce, Saint-Chéron (FR); Sandrine Cappronnier, Massey (FR); Marjorie Lebarbenchon, Egly (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 125 days.

(21) Appl. No.: 16/349,559

(22) PCT Filed: Nov. 15, 2016

(86) PCT No.: PCT/EP2016/077620
§ 371 (c)(1),
(2) Date: May 13, 2019

(87) PCT Pub. No.: WO2018/091063
PCT Pub. Date: May 24, 2018

(65) Prior Publication Data
US 2020/0187517 A1 Jun. 18, 2020

(51) Int. Cl.
A23C 9/123 (2006.01)
A23C 11/10 (2021.01)
C12N 1/20 (2006.01)
C12R 1/46 (2006.01)

(52) U.S. Cl.
CPC .......... *A23C 9/1238* (2013.01); *A23C 11/106* (2013.01); *C12N 1/205* (2021.05); *A23Y 2220/15* (2013.01); *A23Y 2240/75* (2013.01); *A23Y 2300/00* (2013.01); *C12R 2001/46* (2021.05)

(58) Field of Classification Search
CPC ........................... A23C 9/1238; A23C 11/106
See application file for complete search history.

(56) References Cited

U.S. PATENT DOCUMENTS

2003/0091694 A1* 5/2003 Remo .................. A23L 11/09
426/52
2015/0086675 A1* 3/2015 Johansen ............. C12N 15/746
426/43

FOREIGN PATENT DOCUMENTS

WO WO 2013/160413 A1 10/2013
WO WO 2015/193459 A1 12/2015

OTHER PUBLICATIONS

Written Opinion and the International Search Report for International Application No. PCT/EP2016/077620, dated Feb. 1, 2017.
Sorensen, K.I., et al., "Enhancing the Sweetness of Yoghurt through Metabolic Remodeling of Carbohydrate Metabolism in *Streptococcus thermophilus* and *Lactobacillus delbrueckii* subsp. *bulgaricus*", Applied and Environmental Microbiology, vol. 82, No. 12, pp. 3683-3692, Jun. 2016.

* cited by examiner

*Primary Examiner* — Stephanie A Cox
(74) *Attorney, Agent, or Firm* — Arent Fox LLP (57) ABSTRACT

The present invention relates to novel strains of *Streptococcus thermophilus*, compositions comprising said strains and to methods for the preparation of such compositions.

19 Claims, 6 Drawing Sheets

STREPTOCOCCUS THERMOPHILUS FOR USE IN PREPARATION OF FERMENTED PRODUCTS

CROSS-REFERENCE TO RELATED APPLICATIONS

This application is a 35 U.S.C. 371 National Phase of International Patent Application No. PCT/EP2016/077620, filed on Nov. 15, 2016.

FIELD OF THE INVENTION

The present invention relates to novel strains of *Streptococcus thermophilus*, compositions comprising said strains and to methods for the preparation of such compositions.

TECHNICAL BACKGROUND

*Streptococcus thermophilus* (also referred to as *Streptococcus salivarius* subsp. *thermophilus* and hereinafter also referred to as *S. thermophilus*) is a gram positive lactic acid bacterium that is widely used in the preparation of fermented milk products. *S. thermophilus* is commonly used together with *Lactobacillus delbrueckii* subsp. *bulgaricus* (also referred to as *L. bulgaricus*) as a starter culture to prepare yogurt and other types of fermented milks. Yogurts and other fermented milk products are widely consumed and contribute to a healthy diet by providing essential nutrients. However unflavoured fermented milk products have characteristic tart or acidic flavours, thus flavoured and sweetened fermented milk products are popular. Increasing consumer awareness of the benefits of a low-sugar diet together with a trend towards what the consumer perceives as "natural" products has led to a need for the development of fermented milk products with a reduced sugar content that use natural sweetening agents (e.g. stevia). The use of high sugar producing strains of *S. thermophilus* and *L. Bulgaricus* strains has also been proposed as a means of increasing the sweetness of fermented milk products.

WO 2013/160413 discloses mutant *S. thermophilus* strains having sweetening properties due to their secretion of glucose. These strains are characterized by a mutation in the glucokinase (glcK) gene and are described as being suitable for use in the preparation of fermented milk products. However, it is also disclosed that for such strains the fermentation process is delayed by 2-5 hours requiring at least 20 hours of fermentation. Sorensen et al. (Appl Environ Microbiol. 2016 Apr. 22) also disclose glucose secreting *S. thermophilus* strains St1-GS-1; St1-GS-2; St2-GS-1; St2-GS-2. Strains St1-GS-2 and St2-GS-2 could not acidify milk and glucokinase mutant strains (i.e. St1-GS-1 and St2-GS-1) displayed a lag of 2-3 hours over the parent strains in onset of acidification.

SUMMARY OF THE INVENTION

The present invention follows from the unexpected finding that novel strains of *Streptococcus thermophilus* CNCM I-5030 and CNCM I-4992 have sweetening properties, additionally these strains are exceptionally useful in the preparation of fermented milk products due to their milk acidification properties as well as the reduced post-acidification of said fermented milk products. Accordingly, the present invention provides *Streptococcus thermophilus* strains deposited at the CNCM under reference numbers CNCM I-5030 and CNCM I-4992. The present invention also provides compositions comprising *S. thermophilus* CNCM I-5030 and/or CNCM I-4992 and methods for the preparation thereof.

DETAILED DESCRIPTION OF THE INVENTION

As used herein the term "stable composition" shall be taken to mean a composition that does not present sedimentation and/or serum separation.

As used herein the term "x % (w/w)" is equivalent to "x g per 100 g". As used herein the terms "dairy composition", "milk-based composition" or "dairy product" shall be taken to mean a product or composition comprising essentially of or consisting of milk or milk components and optionally further ingredients.

As used herein the term "fermented dairy" shall be taken to mean a product or composition that is the product of the acidifying fermentation of a milk-based composition by a starter culture of fermenting microorganisms, in particular bacteria, preferably lactic acid bacteria. As used herein the term "fermented milk" shall be taken to mean a product or composition derived from milk by the acidifying action of at least one lactic acid bacterium. Accordingly, as used herein a fermented dairy product can thus be a fermented milk, such as a yoghurt (e.g. a set, stirred or drink yogurt), or a fresh cheese such as a white cheese or a "petit-Suisse". It can be also be a strained fermented milk such as a strained yoghurt (e.g. a concentrated or Greek-style yoghurt).

The terms "fermented milk" and "yogurt" or "yoghurt" are given their usual meanings in the field of the dairy industry, that is, products suitable for human consumption and originating from acidifying lactic fermentation of a milk substrate. These products can contain secondary ingredients such as fruits, vegetables, sugar, etc. The expression "fermented milk" may be used to refer to fermented milks other than yogurts e.g. "Kefir", "Kumtss", "Lassi", "Dahi", "Leben", "Filmjolk", "Villi", "Acidophilus milk".

The term "yogurt" or "yoghurt" as used herein shall be taken to mean fermented milk obtained by the acidifying lactic fermentation of specific thermophilic lactic acid bacteria such as *Lactobacillus delbrueckii* subsp. *bulgaricus* and *Streptococcus thermophilus* (also referred to as *Streptococcus salivarius* subsp. *thermophilus*), which must be in the living state in the finished product at a minimum CFU. In certain countries, regulations allow the addition of further lactic acid bacteria to yoghurt such as but not limited to strains of *Bifidobacterium* and/or *Lactobacillus acidophilus* and/or *Lactobacillus casei*. These additional lactic acid bacteria strains are intended to impart various properties to the finished product, such as that of providing organoleptic qualities, favoring equilibrium of intestinal flora or modulating the immune system.

As used herein the term "strained fermented dairy composition" shall be taken to mean a fermented dairy composition which has been subjected to a post-fermentation acid whey separation process.

As used herein the term "spoonable" shall be taken to mean a solid or semi-solid that may be consumed by means of a spoon or other utensil.

As used herein the term "fermentation" shall be taken to mean the metabolism of a substance by microorganisms, e.g. bacteria, yeasts, or other microorganisms.

As used herein the term "cfu" or "CFU" shall be taken to be an abbreviation of the term "colony forming unit".

As used herein the term "CNCM I-" followed by a 4 digit number shall be taken to refer to a strain deposited at the Collection Nationale de Cultures de Microorganismes (CNCM) 25 rue du Docteur Roux, Paris, France under the Budapest Treaty with an accession number corresponding to said 4 digit number, e.g. CNCM I-5030.

As used herein reference to a bacterial strain or species shall be taken to include functionally equivalent bacteria derived therefrom such as but not limited to mutants, variants or genetically transformed bacteria. These mutants or genetically transformed strains can be strains wherein one or more endogenous gene(s) of the parent strain has (have) been mutated, for instance to modify some of their metabolic properties (e.g., their ability to ferment sugars, their resistance to acidity, their survival to transport in the gastrointestinal tract, their post-acidification properties or their metabolite production). They can also be strains resulting from the genetic transformation of the parent strain to add one or more gene(s) of interest, for instance in order to give to said genetically transformed strains additional physiological features, or to allow them to express proteins of therapeutic or prophylactic interest that one wishes to administer through said strains. These mutants or genetically transformed strains can be obtained from the parent strain by means of conventional techniques for random or site-directed mutagenesis and genetic transformation of bacteria, or by means of the technique known as "genome shuffling". In the present text, strains, mutants and variants derived from a parent species or strain will be considered as being encompassed by reference to said parent species or strain, e.g. the phrases "*Streptococcus thermophilus*" and "CNCM I-5030" shall be taken to include strains, mutants and variants derived therefrom. Accordingly, as used herein reference to a bacterial strain specified by an accession or deposit number shall be taken to encompass variants thereof having at least 95% identity (see: Stackebrandt & Goebel, 1994, Int. J. Syst. Bacteriol. 44:846-849). In a particularly preferred embodiment, said variant has at least 97% identity with the 16S rRNA sequence of said specified strain, more preferably at least 98% identity, more preferably at least 99% or more identity.

As used herein the term "substantially pure" when used in reference to a bacterial strain refers to the percent of said bacterial strain relative to the total micro-organism content. Substantially pure can be at least about 99.99%, at least about 99.90%, at least about 99.50%, at least about 99.00%, at least about 95.00%, at least about 90.00%, at least about 35.00%, or at least about 75.00%.

As used herein, a "lactic acid bacterium" is a Gram-positive, acid-tolerant, generally non-sporulating and non-respiring, either rod- or cocci-shaped bacterium that is able to ferment sugars into lactic acid.

The present invention relates to novel strains of *Streptococcus thermophilus*, compositions comprising said strain and to methods for the preparation of such compositions.

*Streptococcus Thermophilus*

In a first aspect the present invention provides strains of *Streptococcus thermophilus*. In a first embodiment the present invention provides the strain *Streptococcus thermophilus* CNCM I-5030. This strain has been deposited at the Collection Nationale de Cultures de Microorganismes (CNCM) (Institut Pasteur, 25 Rue du Docteur Roux, Paris, France) under the Budapest Treaty on 26, Nov. 2015 under reference number CNCM I-5030. The deposit was made in accordance with the Budapest Treaty on the International Recognition of the Deposit of Microorganisms for the Purposes of Patent Procedure, as provided therein the applicant requests that a sample of the deposited micro-organisms only be made available to an independent expert, until the date on which the patent may be granted. In one embodiment the present invention provides the isolated strain *Streptococcus thermophilus* CNCM I-5030, preferably said isolate is substantially pure.

In a second embodiment the present invention provides the strains *Streptococcus thermophilus* CNCM I-4992. This strain has been deposited at the Collection Nationale de Cultures de Microorganismes (CNCM) (Institut Pasteur, 25 Rue du Docteur Roux, Paris, France) under the Budapest Treaty on 1, Jul. 2015 under reference number CNCM I-4992. The deposit was made in accordance with the Budapest Treaty on the International Recognition of the Deposit of Microorganisms for the Purposes of Patent Procedure, as provided therein the applicant requests that a sample of the deposited micro-organisms only be made available to an independent expert, until the date on which the patent may be granted. In one embodiment the present invention provides the isolated strain *Streptococcus thermophilus* CNCM I-4992, preferably said isolate is substantially pure.

Compositions of the Invention

In a second aspect the present invention provides compositions comprising *Streptococcus thermophilus* CNCM I-5030 and/or CNCM I-4992. Preferably, the composition comprises at least $10^6$, more preferably at least $10^7$ and most preferably at least $10^8$ colony forming unit (CFU) *Streptococcus thermophilus* CNCM I-5030 and/or CNCM I-4992 per gram (g) of composition according to embodiments of the invention.

In embodiments, the composition comprises $10^5$ to $10^{12}$ colony forming unit (CFU) *Streptococcus thermophilus* CNCM I-5030 and/or CNCM I-4992 per gram (g) of composition according to embodiments of the invention. In further embodiments, the composition comprises $10^6$ to $10^{11}$ colony forming unit (CFU) *Streptococcus thermophilus* CNCM I-5030 and/or CNCM I-4992 per gram (g) of composition according to embodiments of the invention.

The bacterium as provided herein is suitable for use in edible compositions, accordingly in one embodiment the present invention provides a composition suitable for human consumption or ingestion, preferably by oral means. Accordingly the composition comprises or consists of comestible matter. It is particularly preferred that the compositions of embodiments of the invention are substantially free of pathogenic or toxicogenic matter. The composition according to embodiments of the invention may be a medicament or pharmaceutical composition. In a particularly preferred embodiment the composition according to the invention may be a non-therapeutic composition, preferably a nutraceutical composition, a nutritional composition and/or a food composition. It is particularly preferred that the food composition is a fermented food composition, preferably a fermented dairy composition. Further compositions according to embodiments of the invention also include food additives, food ingredients, nutritional formulas, baby foods, infant milk formulas and infant follow-on formulas.

The composition may comprise further additional strains of *Bifidobacterium* and/or lactic acid bacteria; typically 2, 3, 4 or more additional strains. Examples of *Bifidobacterium* that can be used include but are not limited to *Bifidobacterium animalis* (for example *Bifidobacterium animalis* subsp. *animalis* or *Bifidobacterium animalis* subsp. *lactis*); *Bifidobacterium longum*; *Bifidobacterium breve*; *Bifidobacterium bifidum*. Examples of lactic acid bacteria that can be used include but are not limited to *Lactobacilli* (for example *Lactobacillus acidophilus, Lactobacillus buchneri, Lactobacillus delbruckei*, in particular *L. delbrueckii* subsp. *bul-*

*garicus* or *lactis, Lactobacillus casei, Lactobacillus plantarum, Lactobacillus reuteri, Lactobacillus johnsonii, Lactobacillus helveticus, Lactobacillus brevis, Lactobacillus rhamnosus*); *Lactococci* (for example *Lactococcus lactis*, typically *Lactococcus lactis* subsp. *lactis* or *Lactococcus lactis* subsp. *cremoris*). Preferably the composition further comprises *Lactobacillus* and/or *Streptococcus*. For the preparation of yogurt, the composition typically comprises *Lactobacillus bulgaricus* (also referred to as *Lactobacillus delbrueckii* subsp. *bulgaricus*) and *Streptococcus thermophilus*, optionally with additional microorganisms such as but not limited to probiotic species or other species that may provide desirable organoleptic or other qualities to the composition, e.g. further strains of *Lactococcus lactis*.

Accordingly in one embodiment the present invention provides a composition comprising *Streptococcus thermophilus* CNCM I-5030 and/or CNCM I-4992 and further comprising at least one strain of *Lactobacillus bulgaricus* and optionally one or more strains of *Lactococcus lactis* and/or *Bifidobacterium*.

Dairy Compositions.

The strains of the present invention are particularly suited to the preparation of fermented compositions. Accordingly, In one embodiment the present invention provides a dairy composition, preferably a fermented dairy composition. The dairy composition of the invention comprises milk, preferably fermented milk. Preferably the composition comprises at least about 30% (w/w) milk, more preferably at least about 50% (w/w) milk and even more preferably at least about 70% (w/w) milk. In embodiments, the composition comprises at 30% to 100% (w/w) milk. In embodiments, the composition comprises 50% to 100% (w/w) milk. In embodiments, the composition comprises 70% to 100% (w/w) milk. Preferably said milk is vegetal and/or animal milk, more preferably soya, almond, oat, hemp, spelt, coconut, rice, goat, ewe, camel, mare or cow milk, and most preferably to cow milk. Preferably said milk(s) are heat-treated, typically pasteurized, to ensure sterility. Preferably said heat treatment is carried out prior to the preparation of the fermented dairy composition.

Preferably said milk comprises one or more of skimmed, partially-skimmed or non-skimmed milk. Preferably said milk or milks may be in liquid, powdered and/or concentrated form. In one embodiment said milk further comprises milk components preferably selected from the group consisting of cream, casein, caseinate (for example calcium or sodium caseinate), whey proteins notably in the form of a concentrate (WPC), milk proteins notably in the form of a concentrate (MPC), milk protein hydrolysates, and mixtures thereof. In one embodiment said mixture further comprises plant and/or fruit juices. In one embodiment said milk or milks may be enriched or fortified with further milk components or other nutrients such as but not limited to vitamins, minerals, trace elements or other micronutrients.

Preferably the dairy composition comprises above about 0.3 g per 100 g by weight free lactic acid, more preferably above about 0.7 g or 0.6 g per 100 g by weight free lactic acid. In embodiments, the composition comprises 0.3 g to 0.7 grams per 100 g by weight free lactic acid.

Preferably the dairy composition comprises a protein content at least equivalent to that of the milk or milks from which it is derived, preferably at least about 2.5%, more preferably at least about 3% or 3.5% (w/w). Preferably the composition has a pH equal to or lower than 5, preferably between about 3 and about 4.5 and more preferably between about 3.5 and about 4.5.

Preferably the dairy composition has a viscosity lower than 200 mPa·s, more preferably lower than 100 mPa·s and most preferably lower that 60 mPa·s, at 10° C., at a shear rate of 64 s$^{-1}$. In embodiments, the composition has a viscosity range of 1 to 200 mPa·s, 1 to 100 mPa·s, or 1 to 60 mPa·s, at 10° C., at a shear rate of 64 s$^{-1}$. In embodiments, the composition has a viscosity range of 10 to 200 mPa·s, 10 to 100 mPa·s, or 10 to 60 mPa·s, at 10° C., at a shear rate of 64 s$^{-1}$. In embodiments, the composition has a viscosity range of 30 to 200 mPa·s, 30 to 100 mPa·s, or 30 to 60 mPa·s, at 10° C., at a shear rate of 64 s$^{-1}$.

The fermented dairy composition according to embodiments of the invention is preferably a product selected from the group comprising yogurt, set yogurt, stirred yogurt, pourable yogurt, yogurt drink, frozen yogurt, kefir, buttermilk, quark, sour cream, fresh cheese and cheese. In one embodiment the composition according to embodiments of the invention is a drinkable composition, more preferably a fermented milk drink such as but not limited to a yogurt drink, kefir etc. In an alternative embodiment the composition according to embodiments of the invention is a composition that is spoonable, such as a set or stirred yogurt or equivalent thereof.

In one embodiment the fermented dairy composition is a strained fermented dairy composition. The strained fermented dairy composition preferably has the following contents (% by weight):

from 8.5% to 11.0% of milk protein
from 0.0% to 8.0% of fat, for example from 0.0% to 3.5% or from 3.5% to 8.0%
from 0.00% to 4.20% of lactose, for example from 2.80% to 4.20%

The pH of the strained fermented dairy composition can for example be of from 3.80 to 4.65.

Preferably the composition, according to embodiments of the invention, may be stored, transported and/or distributed at a temperature of from 1° C. to 10° C. for at least about 30 days, at least about 60 days or at least about 90 days from packaging and remain suitable for consumption.

In embodiments, the dairy compositions of the invention comprise at least $10^5$ cfu/g, more preferably at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g *Streptococcus thermophilus* CNCM I-5030 and/or CNCM I-4992 per gram of dairy composition. In embodiments, the compositions of the invention comprise $10^5$ to $10^{12}$ or $10^6$ to $10^{10}$ colony forming unit (CFU) *Streptococcus thermophilus* CNCM I-5030 and/or CNCM I-4992 per gram of composition.

Preferably, the composition is a packaged product that comprises at least $10^6$, more preferably at least $10^7$ and most preferably at least $10^8$ colony forming unit (CFU) *Streptococcus thermophilus* CNCM I-5030 and/or CNCM I-4992 per gram (g) of composition according to embodiments of the invention subsequent to storage, transport and/or distribution at a temperature of from 1° C. to 10° C. for at least about 30 days, at least about 60 days or at least about 90 days from packaging.

In embodiments, the composition is a packaged product that comprises $10^5$ to $10^{12}$ or $10^6$ to $10^{10}$ colony forming unit (CFU) *Streptococcus thermophilus* CNCM I-5030 and/or CNCM I-4992 per gram (g) of composition according to embodiments of the invention subsequent to storage, transport and/or distribution at a temperature of from 1° C. to 10° C. for at least about 30 days, at least about 60 days or at least about 90 days from packaging.

In embodiments, the dairy composition further comprises an intermediate preparation. Intermediate preparations are known to the one skilled in the art. They are typically used to modify the taste, mouthfeel and/or texture of a dairy composition, for example of a fermented dairy composition. They can used also to introduce some additives such as nutrients. They typically comprise sweetening agents, flavors, color modifiers, cereals and/or fruit. Intermediate fruit preparations are for example slurries or fruit preparations. Flavors include for example fruit flavors, vanilla flavors, caramel flavors, coffee flavors, chocolate flavors.

Fruit preparations typically comprise fruits, as used herein the term "fruit" refers to any fruit form, including for example full fruits, pieces, purees, concentrates, juices etc.

The intermediate preparation or slurry typically comprises a stabilizing agent, having at least one stabilizer. The stabilizing agent can comprise at least two stabilizers. Such stabilizers are known to the one skilled in the art. They typically help in avoiding phase separation of solids, for examples of fruits or fruits extracts and/or in avoiding syneresis. They typically provide some viscosity to the composition, for example a viscosity (Bostwick viscosity at 20° C.) of from 1 to 20 cm/min, preferably of from 4 to 12 cm/min.

The stabilizing system or the stabilizer can for example be a starch, a pectin, a guar, a xanthan, a carrageenan, a locust bean gum, or a mixture thereof. The amount of stabilizing system is typically of from 0.5 to 5% by weight.

The intermediate preparation can typically comprise organoleptic modifiers. Such ingredients are known by the one skilled in the art.

The organoleptic modifiers can be for example sweetening agents different from sugar, coloring agents, cereals and/or cereal extracts.

Examples of sweetening agents are ingredients referred to as High Intensity Sweeteners, such as sucralose, acesulfamK, aspartame, saccharine.

Examples of fruits include for example strawberry, peach, apricot, mango, apple, pear, raspberry, blueberry, blackberry, passion, cherry, and mixtures or associations thereof, such as peach-passion.

The fruits can be for example provided as:
frozen fruit cubes, for example 10 mm fruit cubes, for example Individual Quick Frozen fruit cubes, for example strawberry, peach, apricot, mango, apple, pear fruit cubes or mixtures thereof,
Aseptic fruit cubes, for example 10 mm fruit cubes, for example strawberry, peach, apricot, mango, apple or pear fruit cubes or mixtures thereof,
fruit purees, for example fruit purees concentrated from 2 to 5 times, preferably 3 times, for example aseptic fruit purees, for example strawberry, peach, apricot, mango, raspberry, blueberry or apple fruit purees or mixtures thereof,
single aseptic fruit purees, for example strawberry, raspberry, peach, apricot, blueberry or apple single aseptic fruit purees or mixture thereof,
frozen whole fruits, for example Individual Quick Frozen whole fruits, for example blueberry, raspberry or blackberry frozen whole fruits, or mixtures thereof,
mixtures thereof.

The ingredients and/or components of the intermediate preparation and the amounts thereof can be typically such that the composition has a brix degree of from 1 to 65 brix, for example from 1 to 10 brix, or from 10 to 15 brix, or from 15 to 20 brix, or from 20 to 25 brix, or from 25 to 30 brix, or from 30 to 35 brix, or from 35 to 40 brix, or from 40 to 45 brix, or from 45 to 50 brix, or from 50 to 55 brix, or from 55 to 60 brix, or from 55 to 60 brix, or from 60 to 65 brix.

A fruit preparation can for example comprise fruit in an amount of from 30% to 80% by weight, for example from 50 to 70% by weight.

The intermediate preparation can comprise water. It is mentioned that a part of the water can come from ingredients used to prepare the fruit preparation, for example from fruits or fruit extracts or from a phosphoric acid solution.

The fruit preparation can comprise pH modification agents such as citric acid. The fruit preparation can have a pH of from 2.5 to 5, preferably of from 2.8 to 4.2.

Typically a fruit preparation can be added in an amount of 5-35% by weight with reference to the total amount of composition. In embodiments the composition of the invention comprises up to about 30% (w/w) of said intermediate preparation, e.g. up to about 10%, 15%, 20%, 25% (w/w). In one embodiment, the composition according to embodiments of the invention comprise 1% to 30% (w/w) of said intermediate preparation. In alternative embodiments, the composition according to embodiments of the invention comprise 1% to 25% (w/w) of said intermediate preparation. In further alternative embodiments, the composition according to embodiments of the invention comprise 1% to 20% (w/w) of said intermediate preparation. In additional embodiments, the composition according to embodiments of the invention comprise 1% to 15% (w/w) of said intermediate preparation. In further additional embodiments, the composition according to embodiments of the invention comprise 1% to 10% (w/w) of said intermediate preparation.

Preferably the composition, according to embodiments of the invention is provided in a sealed or sealable container containing about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g, 320 g or 500 g or about 1 oz, 2 oz, 3 oz, 4 oz, 5 oz, 6 oz or 12 oz product by weight.

In embodiments, the composition, according to embodiments of the invention is provided in a sealed or sealable container containing about 50 g to 500 g, 60 g to 500 g, 70 g to 500 g, 75 g to 500 g, 80 g to 500 g, 85 g to 500 g, 90 g to 500 g, 95 g to 500 g, 100 g to 500 g, 105 g to 500 g, 110 g to 500 g, 115 g to 500 g, 120 g to 500 g, 125 g to 500 g, 130 g to 500 g, 135 g to 500 g, 140 g to 500 g, 145 g to 500 g, 150 g to 500 g, 200 g to 500 g, 300 g to 500 g, 320 g to 500 g or 500 g product by weight. In embodiments, the composition, according to embodiments of the invention is provided in a sealed or sealable container containing about 1 oz to 12 oz, 2 oz to 12 oz, 3 oz to 12 oz, 4 oz to 12 oz, 5 oz to 12 oz, 6 oz to 12 oz or 12 oz product by weight.

Inoculum Compositions

The bacterium as described herein is useful as starter culture in the preparation of food compositions, such as fermented dairy products. Accordingly, in one embodiment the present invention provides an inoculum comprising *Streptococcus thermophilus* CNCM I-5030 and/or CNCM I-4992 that is suitable for the preparation of fermented dairy products. The inoculum of the invention is suitable for the direct inoculation *Streptococcus thermophilus* CNCM I-5030 and/or CNCM I-4992 into a composition comprising milk to provide fermented dairy products of the invention, typically without the need for a culture step prior to the said direct inoculation.

Typically the inoculum further comprises excipient or carriers, the selection of which is within the scope of the skilled person but may include buffers or culture media. The inoculum may optionally comprise further components such as cryoprotectants, preservatives and/or additives including nutrients such as yeast extracts, cysteine, sugars and vitamins.

Typically the inoculum is for use in the preparation of fermented dairy products, according in one embodiment the inoculum of the invention may be provided to the dairy composition in quantities of up to about 500 mg/l.

Typically the inoculum is fresh, frozen, dried or lyophilized. The inoculum may be in liquid, dry, spray-dried or solid form. It is particularly preferred that the inoculum is in liquid form. The inoculum may be defrosted and/or dispersed in liquid (e.g. water) prior to inoculation into a composition comprising milk.

In embodiments, the inoculum comprises at least $10^9$ cfu, e.g. at least $10^{10}$ cfu, such as at least $10^{11}$ cfu *Streptococcus thermophilus* CNCM I-5030 and/or CNCM I-4992 per gram of inoculum composition. In embodiments, the inoculum comprises $10^9$ to $10^{12}$ colony forming unit (CFU), or more preferably $10^{10}$ to $10^{12}$ colony forming unit (CFU) *Streptococcus thermophilus* CNCM I-5030 and/or CNCM I-4992 per gram of inoculum.

Preferably the inoculum comprising *Streptococcus thermophilus* CNCM I-5030 or CNCM I-4992 is substantially pure.

In a further embodiment the present invention provides a mixture or kit of parts of the inoculum of the invention together with inoculum of *Bifidobacterium* and/or lactic acid bacteria.

Examples of *Bifidobacterium* that can be used include but are not limited to *Bifidobacterium animalis* (for example *Bifidobacterium animalis* subsp. *animalis* or *Bifidobacterium animalis* subsp. *lactis*); *Bifidobacterium longum*; *Bifidobacterium breve*; *Bifidobacterium bifidum*. Examples of lactic acid bacteria that can be used include but are not limited to *Lactobacilli* (for example *Lactobacillus acidophilus, Lactobacillus buchneri, Lactobacillus delbrueckii,* in particular *L. delbrueckii* subsp. *bulgaricus* or *lactis, Lactobacillus casei, Lactobacillus plantarum, Lactobacillus reuteri, Lactobacillus johnsonii, Lactobacillus helveticus, Lactobacillus brevis, Lactobacillus rhamnosus*); *Lactococci* (for example *Lactococcus lactis*, typically *Lactococcus lactis* subsp. *lactis* or *Lactococcus lactis* subsp. *cremoris*). Preferably the inoculum mixture further comprises *Lactobacillus* and/or *Streptococcus*. For the preparation of yogurt, the inoculum mixture typically comprises *Lactobacillus bulgaricus* (also referred to as *Lactobacillus delbruckeii* subsp. *bulgaricus*) and *Streptococcus thermophilus*, optionally with additional microorganisms such as but not limited to probiotic species or other species that may provide desirable organoleptic or other qualities to the composition, e.g. *Lactococcus lactis*.

Accordingly in one embodiment the present invention provides an inoculum mixture comprising a *Streptococcus thermophilus* CNCM I-5030 and/or CNCM I-4992 inoculum and further comprising at least one inoculum of *Lactobacillus bulgaricus* and optionally one or more additional inoculum of *Lactococcus lactis* and/or *Bifidobacterium*.

Methods for the Preparation of Fermented Dairy Products

The bacteria as provided herein are suitable for use in the preparation of fermented dairy products. Accordingly in a third aspect the present invention also relates to the intended use of *Streptococcus thermophilus* CNCM I-5030 and/or CNCM I-4992 for the preparation of a food composition.

The present invention provides a process for the preparation of a fermented dairy product comprising inoculating a milk-based composition with *S. thermophilus* CNCM I-5030 and/or CNCM I-4992 and fermenting.

Accordingly in one embodiment the present invention provides a process comprising the following steps:
i) providing a mixture comprising:
a) milk
b) *Streptococcus thermophilus* CNCM I-5030 and/or CNCM I-4992
ii) fermentation of said mixture to provide a fermented dairy product.

Preferably fermented dairy products are prepared using milk that has been subjected to heat treatment at least equivalent to pasteurization. Preferably said heat treatment is carried out prior to the preparation of the composition.

Typically, milk is pasteurized by means of the following successive steps:
1) standardization of fatty substances of the raw material so as to obtain a standardized substance,
2) enrichment with dried matter of the standardized substance obtained in the preceding stage, so as to obtain an enriched substance,
3) preheating of the enriched substance obtained in the preceding stage, so as to obtain a starting substance,
4) pasteurization and holding of the starting substance obtained in the preceding stage, so as to obtain a pasteurized and held substance,
5) an optional stage of homogenization of the pasteurized and held substance obtained in the preceding stage, so as to obtain a pasteurized, held and optionally homogenized substance,
6) initial cooling of the pasteurized, held and optionally homogenized substance obtained in the preceding stage, so as to obtain a pasteurized starting substance that has been held, optionally homogenized, and cooled down.

As used herein "standardization of fatty substances" is taken to mean a stage of bringing the quantity of fats present in the starting substance to a pre-determined level. Enrichment with dried matter involves the addition of proteins and fatty substance in order to modify curd firmness.

As used herein "holding" is taken to mean a rapid heating and maintenance of temperature of the milk and makes it possible to destroy the vegetative microbial flora, including pathogenic forms. Its typical duration is from 4 to 10 minutes, in particular from 5 to 8 minutes, and in particular approximately 6 minutes.

As used herein "homogenization" is taken to mean the dispersion of the fatty substances in the milk-type substance into small fat globules. The homogenization is carried out for example at a pressure of 100 to 280 bars, in particular 100 to 250 bars, in particular 100 to 200 bars, in particular approximately 200 bars. This homogenization stage is purely optional. It is in particular absent from the production process of products with 0% fatty substances.

Typically a fermented dairy product is prepared by culture of milks at a suitable temperature with suitable microorganisms to provide a reduction in pH, preferably to a pH equal to or lower than 5, preferably between about 3 and 4.7; more preferably between about 3.5 and about 4.7. The pH can be adjusted by controlling the fermentation by the microorganism and stopping it when appropriate, for example by cooling.

According to a further embodiment of the process for the preparation of a fermented dairy product as defined above, the mixture comprising milk and *Streptococcus thermophilus* CNCM I-5030 and/or CNCM I-4992 further comprises at least one, two, three or more strains of *Bifidobacterium* and/or lactic acid bacteria. The selection of suitable *Bifidobacterium* strains is within the scope of the skilled person and is typically a probiotic lactic acid bacteria. Examples of *Bifidobacterium* that can be used include but are not limited to *Bifidobacterium animalis* (for example *Bifidobacterium animalis* subsp. *animalis* or *Bifidobacterium animalis* subsp. *lactis*); *Bifidobacterium longum*; *Bifidobacterium breve*; *Bifidobacterium bifidum*.

The selection of suitable lactic acid bacteria strains is within the scope of the skilled person and is typically a thermophillic lactic acid bacteria. Examples of lactic acid bacteria that can be used include but are not limited to *Lactobacilli* (for example *Lactobacillus acidophilus*, *Lactobacillus buchneri*, *Lactobacillus delbruckeii*, in particular *L. delbrueckii* subsp. *bulgaricus* or *lactis*, *Lactobacillus casei*, *Lactobacillus plantarum*, *Lactobacillus reuteri*, *Lactobacillus johnsonii*, *Lactobacillus helveticus*, *Lactobacillus brevis*, *Lactobacillus rhamnosus*); *Lactococci* (for example *Lactococcus lactis*, typically *Lactococcus lactis* subsp. *lactis* or *Lactococcus lactis* subsp. *cremoris*). Typically a mixture or association of a plurality of species of lactic acid bacteria may be used, typically a mixture or association of *Lactobacillus* and *Streptococcus*. For the preparation of yogurt this typically includes *Lactobacillus bulgaricus* (also referred to as *Lactobacillus delbrueckii* subsp. *bulgaricus*) and *Streptococcus thermophilus*, optionally with additional microorganisms such as but not limited to probiotic species or other species that may provide desirable organoleptic or other qualities to the composition, e.g. *Lactococcus lactis*.

Accordingly in one embodiment the mixture further comprises at least one strain of *Lactobacillus bulgaricus* and optionally one or more strains of *Lactococcus lactis* and/or *Bifidobacterium*.

Suitable temperatures for milk fermentation are typically about 36° C. to about 44° C. and the temperature is maintained for an incubation time sufficient to provide the desired reduction in pH. For the preparation of a fermented dairy product the temperature at the start of fermentation is typically about 36° C. to about 43° C., in particular about 37° C. to about 40° C., the temperature at the end of fermentation is typically about 37° C. to about 44° C., in particular about 38° C. to about 41° C. The fermentation time is typically about 6 to about 11 hours.

Subsequent to the fermentation the fermented milk is cooled. Optionally a stage of intermediate cooling of the fermented milk may be performed to provide a pre-cooled fermented milk having a temperature of between about 22° C. and about 4° C. Typically the intermediate cooling time is about 1 hour to about 4 hours, in particular about 1 hour 30 minutes to about 2 hours. The pre-cooled fermented milk is typically stored for up to 40 hours or less.

Preferably a stage of final cooling of the fermented milk is performed such that the temperature at the start of the final cooling is less than about 22° C. and the temperature at the end of the final cooling is about 4° C. to about 10° C. The cooled product may then be stored, transported and/or distributed at a temperature from about 1° C. to about 10° C. for at least about 30 days, at least about 60 days or at least about 90 days.

According to a further embodiment, the process for the preparation of a fermented dairy product as defined above optionally comprises a stage of stirring at a pressure of at least 20 bars, or performing a dynamic smoothing, to obtain a composition having the desired viscosity, typically a viscosity of up to 20 mPa·s. Stirring or dynamic smoothing operations provide some shear to composition that typically allow a viscosity drop. Such operations are known by the one skilled in the art, and can be operated with conventional appropriate equipment. This stage is typically performed at cold temperature, for example at a temperature of form 1° C. to 20° C. Without intending to be bound to any theory, it is believed that applying some shear at cold temperature, typically by stirring at high pressure or by performing a dynamic smoothing, can lead to a fluid gel formation within the composition, that provides improved stability even at a low viscosity of up to 20 mPa·s.

Alternatively, according to a further embodiment, the process for the preparation of a fermented dairy product as defined above optionally comprises a stage of acid whey removal to provide a "strained fermented dairy composition". In this step an acid whey composition is separated from the curd resulting from the protein coagulation due to acidification during fermentation. Thus one obtains:

a fermented dairy product, typically comprising the proteins coagulum, referred to as a strained fermented dairy composition, and an acid whey by-product Such separation steps are known by the one skilled in art, for example in processes of making "greek yogurts". The separation can for example be carried out by reverse osmosis, ultrafiltration, or centrifugal separation. The separation step can be performed for example at a temperature of from 30° C. to 45° C.

According to a further embodiment, the process for the preparation of a fermented dairy product as defined above optionally comprises a stage of addition of an intermediate preparation as described above prior or subsequent to fermentation, said intermediate preparation typically comprising a preparation of fruits and/or cereals and/or additives such as flavorings and/or colourings.

The invention will be further illustrated by the following non-limiting Figures and Example.

DESCRIPTION OF THE FIGURES

FIG. 3 provides a plot representing fermented milk post-acidification, *S. thermophilus* viability and texturizing properties of a panel of over 40 *S. thermophilus* strains according to Example 2. Post-acidification is represented as dornic acidity increase over 28 day-storage of the fermented on the X-axis. *S. thermophilus* viability as determined by colony forming unit count loss over 28 day-storage is provided on the Y-axis. Each tested strain is represented by a single circular point and classified according to viscosity of the fermented milk, points highlighted in a square have a measured viscosity of <0.25 Pa. S−1, circular points which are not highlighted by a further shape have a viscosity of 0.25-0.5 Pa. S−1, points highlighted in a pentagon have a measured viscosity of 0.5-0.75 Pa. S−1 and points highlighted in a triangle have a measured viscosity of 0.75-1.1 Pa. S−1.

EXAMPLES

A screening of over 40 strains of *S. thermophilus* was carried out to identify strains that were firstly suitable for the preparation of fermented milk products (FMP) but that also have sweetness enhancing properties in such products based on their impact on post-acidification during storage and texturizing properties. Two strains of *S. thermophilus* were selected on the basis of having high viability and good milk acidification properties together with good texturizing capabilities (increased viscosity) and low post-acidification during storage. Sweetness perception enhancing properties of the strains was determined by a tasting panel evaluating two types of FMP.

Example 1

CNCM I-5030 & CNCM I-4992 Milk Acidification and Viability

Reconstituted milk was prepared by mixing 137.5 g skimmed milk powder (Aria) per litre permuted water and pasteurized at 95° C. for 45 minutes, for strain CNCM I-5030 0.5% Vitalarmor 950 (Armor Proteins) was added. Bacterial strains were provided in frozen form by Danone. Strains were inoculated at 1% in the reconstituted milk from a culture obtained in milk enriched by 0.2% of yeast extract, obtained itself by a 1% inoculation of the strain from a first step of culture in M17 medium inoculated by the bacterial strain in frozen form. Fermentation was carried out at 37° C. and monitored using a CINAC pH probe. The resultant fermented milk was cooled and stored at 10° C. for determination of strain viability and post-acidification of the fermented milk over 28 day storage.

*S. thermophilus* strains CNCM I-1630 and CNCM I-2130 used in the preparation of commercially available fermented milk products were used as the benchmarks for CNCM I-5030 and CNCM I-4992 respectively to determine the suitability of strains for use in the preparation of fermented milk food products.

Figure 1:
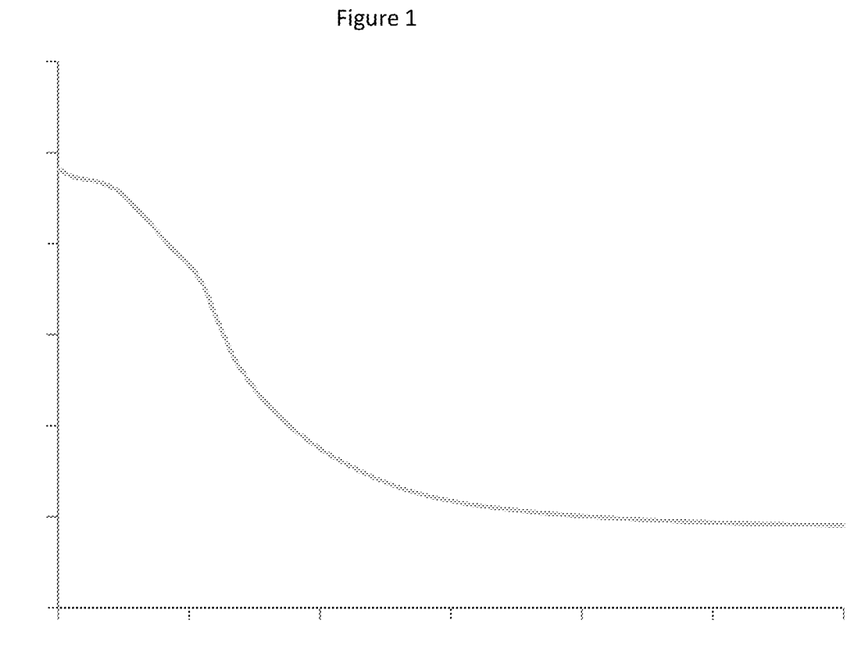
FIG. 1 provides the milk acidification kinetics of *S. thermophilus* strain CNCM I-4992 as determined according to Example 1. Time in minutes is provided on the x-axis, pH is represented on the y-axis.
Figure 2:
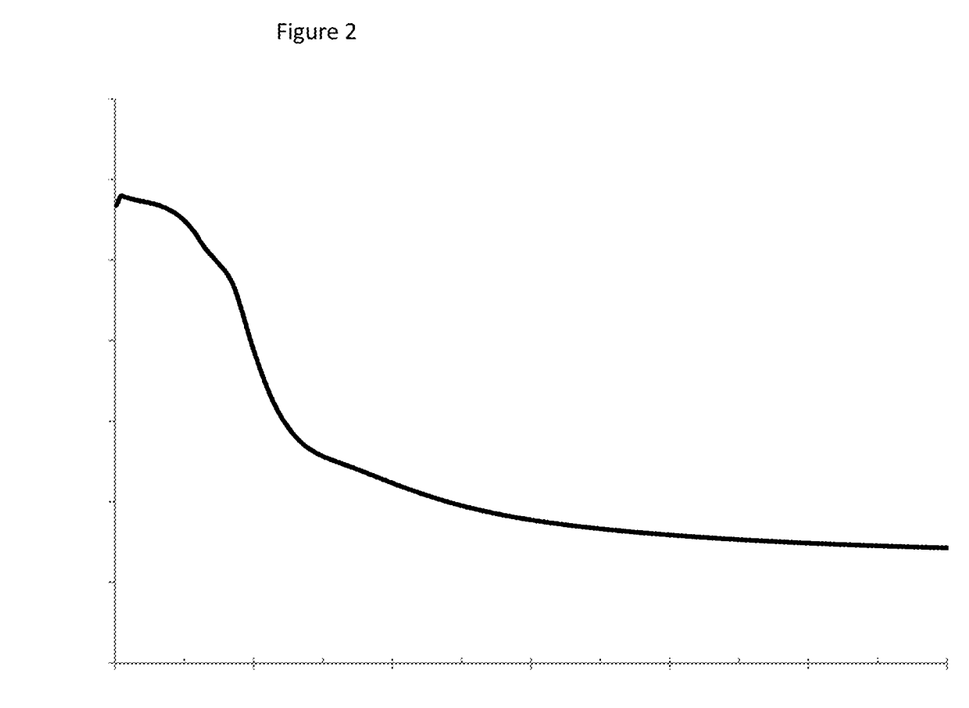
FIG. 2 provides the milk acidification kinetics of *S. thermophilus* strain CNCM I-5030 as determined according to Example 1. Time in minutes is provided on the x-axis, pH is represented on the y-axis.

*Streptococcus thermophilus* strains CNCM I-5030 & CNCM I-4992 demonstrated excellent milk fermentation properties, as illustrated in the acidification curves provided in FIGS. 1 & 2. Milk fermentation properties of the strains were comparable to commercially used strains CNCM I-1630 and CNCM I-2130 respectively for strains CNCM I-5030 & CNCM I-4992.

Example 2

CNCM I-5030 & CNCM I-4992 Fermented Milk Characteristics

Post-acidification affects the taste of fermented milk products and is caused by the continued production of lactic acid by bacterial cultures during the shelf-life of the products. In order to determine the post-acidification properties of the panel of *S. thermophilus* strains fermented milk products were prepared using said strains according to Example 1. The change in dornic acid degree of the fermented milks was determined over 28 day-storage at 10° C. Viability of the *S. thermophilus* strains, as measured by bacterial counts in colony forming units (CFU) was also determined. Finally, texturizing properties of the strains was determined by measuring viscosity. The viscosity was measured by applying a regular shearing strength increase using a rheometer with 2 co-axial cylinders (RM 180, Mettler). Mobile n°1 was used together with the pot n°1. 64 s−1 shearing is applied during 10 seconds on the test product at 10° C.

Figure 3:
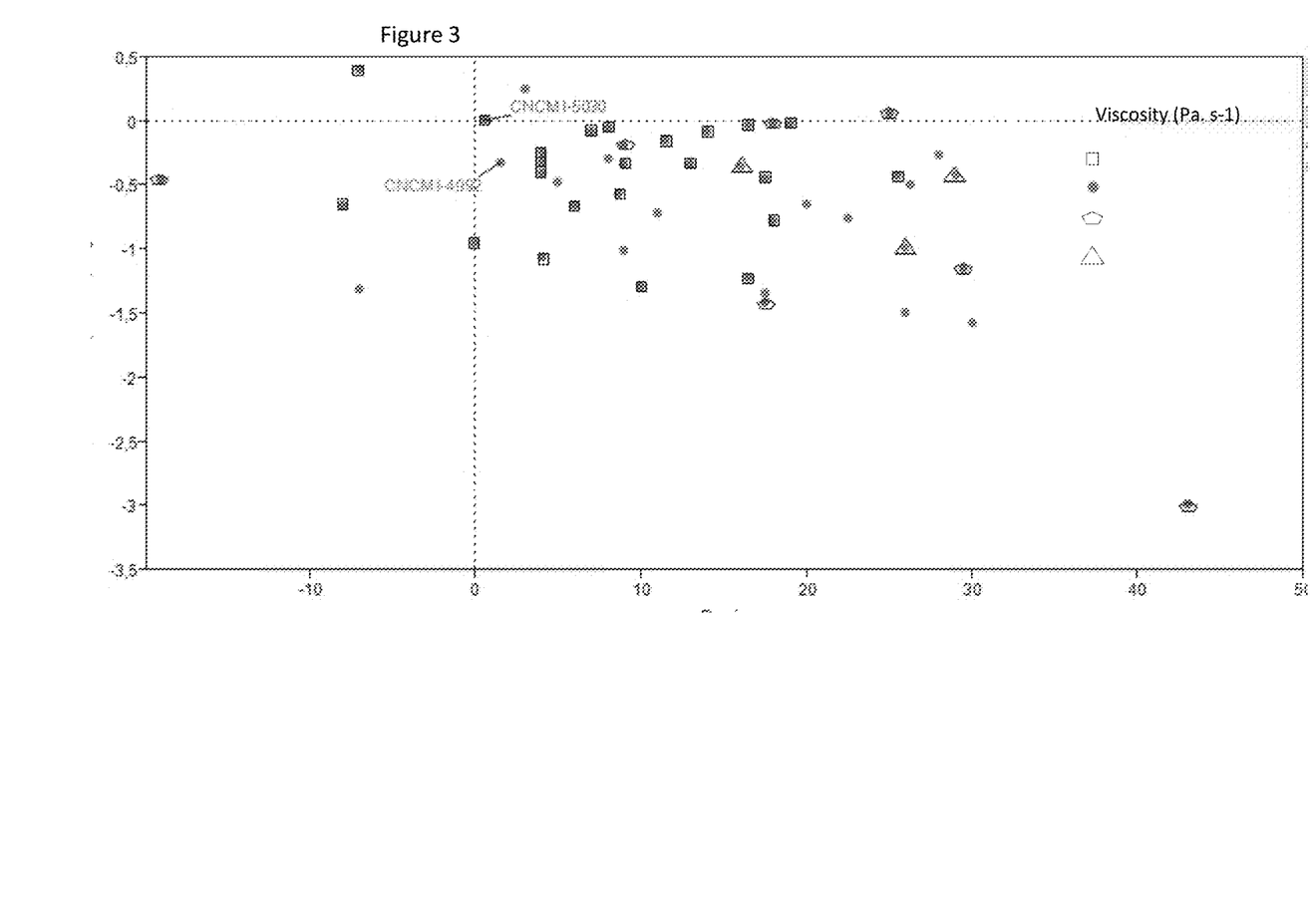

Results are shown in FIG. 3, a change in dornic degree of zero (i.e. no post-acidification) is preferred. Maintenance of *S. thermophilus* bacterial counts was measured by CFU counts at the beginning and end of storage, maintenance of high counts together with low post-acidification are preferred. As demonstrated in FIG. 3, of the tested strains CNCM I-5030 & CNCM I-4992 demonstrated an exceptional combination of post-acidification and texturizing properties as well as good strain viability.

Example 3

Figure 4:
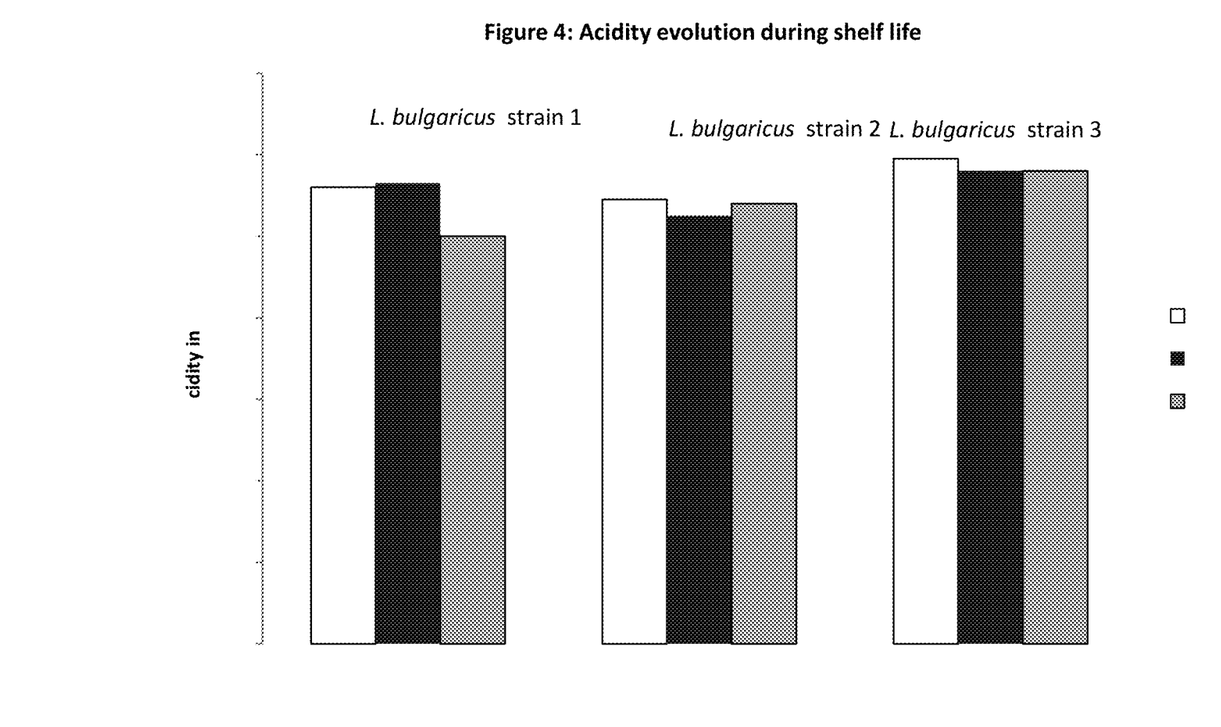
FIG. 4 provides the dornic acidity of test fermented milks according to Example 3. Acidity was measured at 3 time points; Day 0 (white bar), Day 14 (black bar) and Day 28 (grey bar).

FMP starter cultures typically contain an association of *S. thermophilus* and *L. bulgaricus* strains. Accordingly In order to confirm its post-acidification properties strain CNCM I-4992 was tested in association with 3 different strains of *L. bulgaricus*. A food-grade fermented milk product was prepared by fermentation of a pasteurized milk base (13.75% cow skim milk powder in permuted water and pasteurized at 95° C. for 45 minutes) with the yogurt starter culture (*L. delbrueckii, S. thermophilus*). Fermentation was carried out at 37° C., and monitored using a CINAC probe. Fermentation was stopped by rapid cooling when pH 4.7 was reached. The change in dornic acid degree of the fermented milks was determined over 28 day-storage at 10° C. As demonstrated in FIG. 4, post-acidification of the fermented milks remained low.

Example 4

Fermented Milk Product Test

Figure 5:
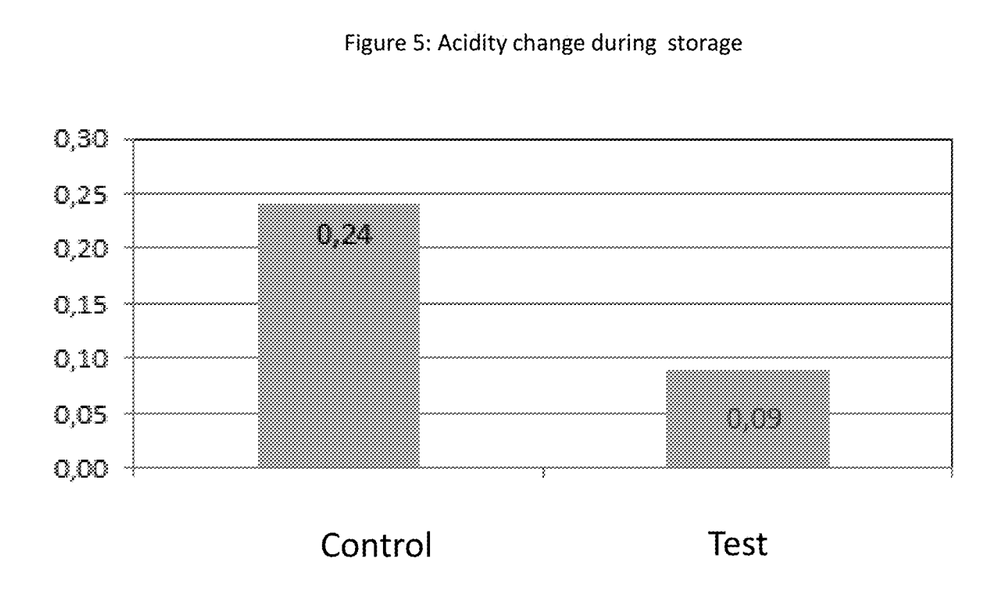
FIG. 5 provides the change in acidity of test and control fermented milks over 28 days according to Example 4.
Figure 6:
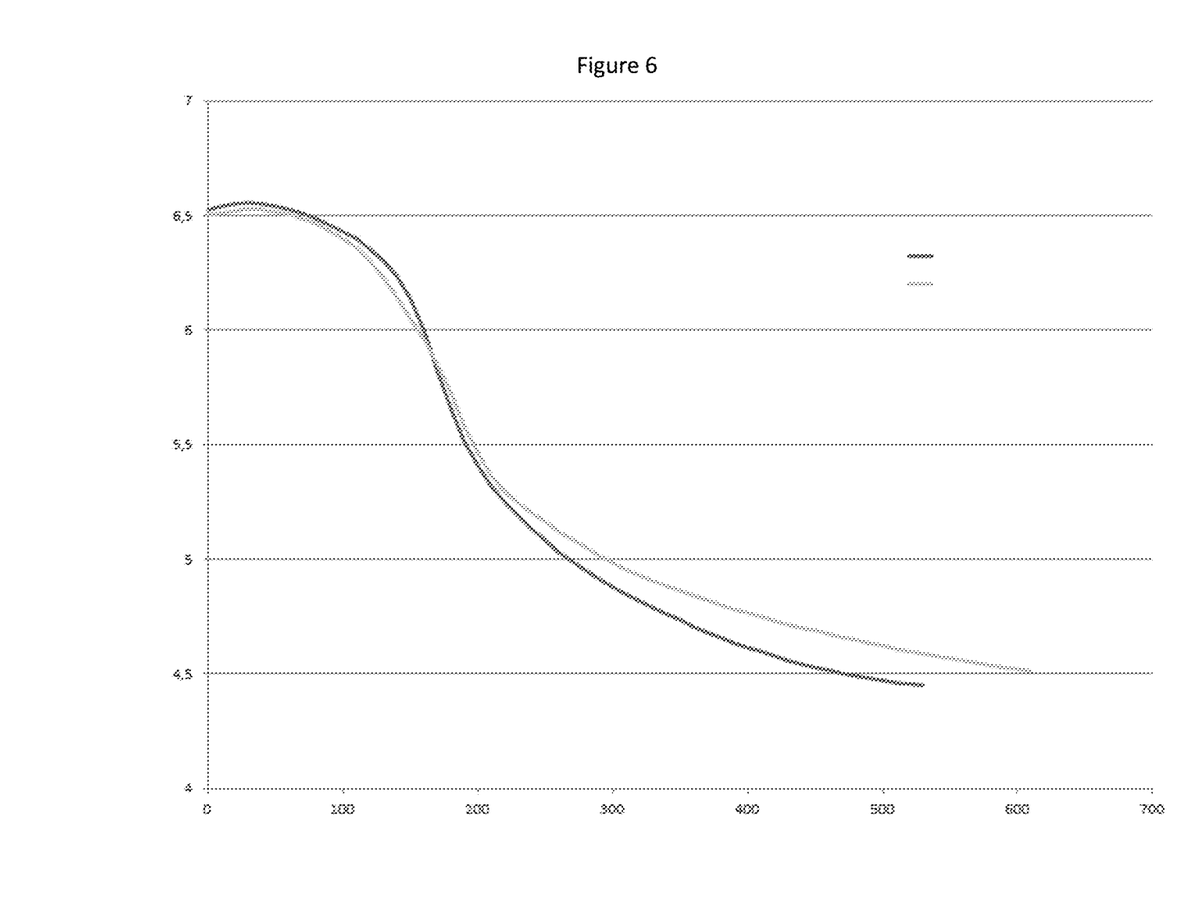
FIG. 6 provides the milk acidification kinetics of test (dark grey) and control (light grey) fermented milks as determined according to Example 4. Time in minutes is provided on the x-axis, pH is represented on the y-axis.

A test fermented milk product starter culture was prepared using strains CNCM I-5030 & CNCM I-4992 together with a *L. bulgaricus* strain (CNCM I-2787) (test product). As a benchmark a yogurt (Vitalinea™) starter culture containing two strains of *S. thermophilus* and *L. bulgaricus* was used (control). Ferments were provided in frozen pellet form and defrosted prior to use at 38° C., the liquid ferment was added to the milk mixture at 0.02% volume. A food-grade fermented milk product was prepared using a homogenized & pasteurized milk mix: 95% milk base (milk, skim milk powder & cream) & 5% sugar and fermenting with the test and control starter cultures. Fermentation was carried out at 38° C. to pH 4.6 (6-7 hours). The resultant fermented milks were smoothed with a mixer (Ystral), cooled to 20° C. and stored at 10° C. for 30 days. The change in dornic acid degree was determined at the end of the storage period. FIG. 6 provides the milk acidification curves of the products prepared using the test (dark grey) and control (light grey) starter cultures, confirming that the favourable acidification kinetics of the test starter culture are comparable to control starter culture. As can be seen in FIG. 5, the test product comprising the strains of the invention had better post-acidification properties.

The qualities of sweetness, acidity, thickness and global dairy notes of Test & benchmark products were assessed by a panel of volunteer testers. Products were tested at days 14 and 28 of storage at 10° C. Fermented milk products prepared using Test starter culture were found to be significantly sweeter than those prepared using benchmark culture.

Example 5

Sweetness Perception Fermented Milk Product

Enhanced sweetness perception of products prepared using the test starter culture according to Example 4 (CNCM I-5030+CNCM I-4992+*L. bulgaricus* strain) as compared to the control starter culture was confirmed in a "fromage frais" (fresh cheese) style calcium-supplemented FMP.

A food-grade fermented milk product was prepared by fermenting a pasteurized milk mix: 93.85% milk base (milk, skim milk powder & cream), starch 1.5%, 4.5% sugar and 0.15% calcium with the test and control starter cultures. Fermentation was carried out at 38° C. to pH 4.6 (6-7 hours). The two products were compared by a panel of volunteers for visual whey, colour, firmness, acidity, fruity intensity, texture in mouth and off notes. No significant differences were found between the test and control products for visual whey, colour, firmness, sweetness, acidity, fruity intensity, texture in mouth and off notes. However increased sweetness was confirmed in the test product, and differences in firmness were also noted.

The invention claimed is:

1. A dairy composition comprising milk and *Streptococcus thermophilus* strain(s) deposited at CNCM under reference number(s) CNCM I-5030 and/or CNCM I-4992.

2. The dairy composition according to claim 1, comprising at least $10^5$ CFU/g of *Streptococcus thermophilus* CNCM I-5030 and/or CNCM I-4992.

3. The dairy composition according to claim 1, wherein said dairy composition is a fermented composition.

4. The dairy composition according to claim 1, further comprising at least one, two, three or more strains of *Bifidobacterium* or lactic acid bacteria.

5. The dairy composition according to claim 4, wherein said dairy composition comprises at least two strains of lactic acid bacteria, wherein said strains of lactic acid bacteria comprise at least one strain of *Lactobacillus bulgaricus*.

6. The dairy composition of claim 4, further comprising one or more strains of *Bifidobacterium*.

7. The dairy composition of claim 1, wherein the milk is vegetal milk.

8. The dairy composition of claim 7, wherein the vegetal milk is soya, almond, oat, hemp, spelt, coconut, or rice milk.

9. The dairy composition of claim 1, wherein the milk is animal milk.

10. The dairy composition of claim 9, wherein the animal milk is goat, ewe, camel, mare or cow milk.

11. The dairy composition according to claim 1, comprising milk and *Streptococcus thermophilus* strain deposited at CNCM under reference number CNCM I-5030.

12. The dairy composition according to claim 1, comprising milk and *Streptococcus thermophilus* strain deposited at CNCM under reference number CNCM I-4992.

13. The dairy composition according to claim 1, comprising milk and *Streptococcus thermophilus* strains deposited at CNCM under reference numbers CNCM I-5030 and CNCM I-4992.

14. The dairy composition of according to claim 13, further comprising *Lactobacillus bulgaricus*.

15. A fermented food product comprising *Streptococcus thermophilus* strain(s) deposited at CNCM under reference number(s) CNCM I-5030 and/or CNCM I-4992.

16. A method for the preparation of a fermented dairy product comprising fermenting a mixture comprising:
  a) milk; and
  b) *S. thermophilus* CNCM I-5030 and/or CNCM I-4992, to provide a fermented dairy product.

17. The method according to claim 16, wherein the mixture comprises at least one, two, three or more strains of *Bifidobacterium* or lactic acid bacteria.

18. The method according to claim 17, further comprising one or more strains of *Bifidobacterium*.

19. The method according to claim 17, wherein the mixture comprises at least two strains of lactic acid bacteria, wherein said strains of lactic acid bacteria comprise at least one strain of *Lactobacillus bulgaricus*.

* * * * *